United States Patent [19]  
Schmitz-Josten et al.

[11] 4,323,348  
[45] Apr. 6, 1982

[54] DENTAL COMPOSITIONS

[75] Inventors: Robert Schmitz-Josten, Cologne; Manfred Borgardt, Wuppertal; Hans-Hermann Schulz, Leichlingen; Michael Walkowiak, Leverkusen, all of Fed. Rep. of Germany

[73] Assignee: Bayer Aktiengesellschaft, Leverkusen, Fed. Rep. of Germany

[21] Appl. No.: 173,945

[22] Filed: Jul. 31, 1980

[30] Foreign Application Priority Data

Aug. 7, 1979 [DE] Fed. Rep. of Germany ....... 2931926

[51] Int. Cl.$^3$ ............................................. A61K 6/08
[52] U.S. Cl. ..................................... 433/228; 106/35; 260/998.11; 433/199; 433/201; 433/202; 524/854; 523/116
[58] Field of Search ............... 433/199, 201, 202, 228; 106/35; 260/42, 998.11

[56] References Cited

U.S. PATENT DOCUMENTS

| | | | |
|---|---|---|---|
| 3,066,112 | 11/1962 | Bowen | 260/41 |
| 3,425,988 | 2/1969 | Gorman | 260/47 |
| 3,629,187 | 12/1971 | Waller | 260/41 |
| 3,709,866 | 1/1973 | Waller | 260/27 R |
| 3,759,807 | 9/1973 | Osborn et al. | 204/159.32 |
| 4,017,454 | 4/1977 | Müller | 260/42.52 |
| 4,089,763 | 5/1978 | Dart et al. | 204/159.23 |

Primary Examiner—Lorenzo B. Hayes  
Attorney, Agent, or Firm—Sprung, Felfe, Horn, Lynch & Kramer

[57] ABSTRACT

The invention relates to the provision of dental compositions containing a polymerizable (meth)acrylic acid ester of the formula Id as defined herein and includes methods for filling or repairing teeth in warm-blooded animals.

17 Claims, No Drawings

DENTAL COMPOSITIONS

The invention relates to novel dental compositions, in particular for dental fillings and dentures, and to their dental use.

It is known to use polymerisable monomers, in particular esters of acrylic acid or methacrylic acid, for the preparation of dental fillings, dental repair materials, dental sealing compositions, dentures and other dental compositions.

Polyfunctional derivatives of acrylic acid or methacrylic acid are frequently used to increase the mechanical properties, such as compressive strength or abrasion resistance. For example, the reaction product, described in U.S. Pat. No. 3,066,112, of 2 mols of glycidyl methacrylate and 1 mol of bisphenol A (called BIS-GMA for short), which is processed together with quartz glass or a similar material, has proved suitable for the peraparation of dental filling compositions. Such products, which are called composite dental filling compositions, usually contain monomer mixtures and up to 80% of an inorganic filler, such as quartz or silicates, pre-treated with adhesion promoters. Silicates of barium, lanthanum, zirconium or other metals with a high atomic number are frequently also added to increase the X-ray opacity.

The compositions are hardened by reactions in which free radicals are formed, such as, for example, by redox polymerisation, or by photopolymerisation in the presence of suitable photoinitiators, as learned from the teachings of, for example, U.S. Pat. 3,629,187 and U.S. Pat. 3,709,866.

In contrast to amalgam fillings, such composite dental filling compositions can be prepared in any desired colour shade, which is of considerable importance particularly in the region of the front teeth.

A large number of monomers other than BIS-GMA have been proposed as being suitable as polymersiable binders for dental compositions, in particular for dental filling compositions and repair compositions, but many of their properties are still in need of improvement; the amalgam fillings are still superior to such composites, in particular in respect of flexural strength and abrasion resistance.

According to the present invention there are provided dental compositions containing a polymerisable (meth)acrylic acid ester of the formula (Id), as defined below, and optionally one or more inert dentally acceptable carriers, including fillers, stabilisers and pigments. Particularly preferred esters of formula (Id) for use in dental compositions of the present invention are those in which R represents

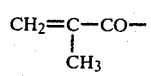

and especially those in which R has this meaning and $R_1$ represents a hydrogen atom or represents a methyl group.

The esters of formula (Id) are, surprisingly, particularly suitable binders for dental compositions. They can be prepared by methods which are in themselves known, by reaction of the tricyclo-decane derivative of formula (Ia) with an alkylene oxide to give a compound of formula (Ic) and subsequent esterification of the compound of formula (Ic) with acrylic acid or methacrylic acid.

Bis-hydroxymethyl-tricyclo$[5.2.1.0.^{2.6}]$-decane (the compound of formula (Ia)) is commercially available under the name TCD-DM. As formula (Ia) shows, it is an isomer mixture, it being possible for the hydroxymethyl groups to be both in the 3- or 4-position and in the 8- or 9-position. The ether-alcohols of the general formula (Ic) are obtained from TCD-DM by adding on alkylene oxides, in particular ethylene oxide, propylene oxide and butylene oxide, in the presence of basic catalysts, and these compounds of the formula (Ic) are then converted into the novel acrylic acid esters or methacrylic acid esters of formula (Id).

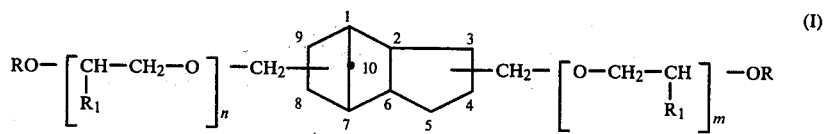

Formulae (Ia), (Ib), (Ic) and (Id) referred to herein correspond to formula (I) given above in which the substituents shown have the following meanings:

I a: $R=H$; $n+m=0$

I b:

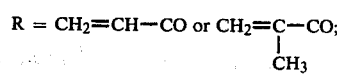

$n+m=0$

I c: $R=H$; $n+m=1-10$; $R_1=H$, $CH_3$ or $C_2H_5$

I d:

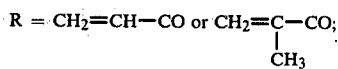

$R_1=H$, $CH_3$ or $C_2H_5$;

$n+m=1-10$.

The acrylic and methacrylic acid esters of formula (Ib), which are free from ether groups, and their use for dental compositions are known from DT-OS (German Published No.) 2,200,021 and DT-OS (German Published No.) 2,816,823, whilst the esters of the formula (Id) are novel. (However, these esters per se and their preparation are the subject of copending and commonly assigned application Ser. No. 174,332 filed Aug. 8, 1980 (Le A 19 805)). Because of their diversity, they present better possibilities for selecting monomers which are better adapted to the particular intended use than is the case with the acrylates of formula (Ib). In particular, they shrink less on polymerisation. Furthermore, as a result of the higher oxygen content, there is an increased absorption of water which is admittedly slight, but controlled, and which further reduces shrinkage on polymerisation. It has furthermore been found that the dental compositions prepared from compounds of formula (Id) have a higher flexural strength than corresponding compositions prepared from compounds of formula (Ib).

As a result of their low viscosity, the monomers of formula (Id) can usually be used without further diluents, which is not possible in the case of BIS-GMA. In contrast, they are suitable as diluents for highly viscous dental binders, such as, for example, BIS-GMA. The low viscosity of the monomer of formula (Id) and its good wetting properties are particularly advantageous for the preparation of coating and sealing compositions.

It is possible to mix the compounds of formula (Id) wherein $R$ is $CH_2=C-CO-$ or $CH_2=CH-CO-$;
         |
         $CH_3$ $R_1$ is H or $-CH_2-OR$; n is 1–4 and m is 0–4, with other known methacrylic acid esters without problems, for example to establish a certain viscosity, a certain refractive index or a desired content of double bonds for the desired intended use. The mixtures shall contain at least 20% of the compounds of formula Id. Polyfunctional monomers, such as ethylene glycol dimethacrylate, triethylene glycol dimethacrylate, trimethylolpropane trimethacrylate, pentaerythritol tetraacrylate, butane-1,3-diol dimethacrylate and hexane-1,6-diol dimethacrylate, are particularly suitable for the preparation of mixed binders containing compounds of formula (Id). Further monomers which are suitable for admixtures containing compounds of formula (Id) are listed, by their formulae, in the summary below:

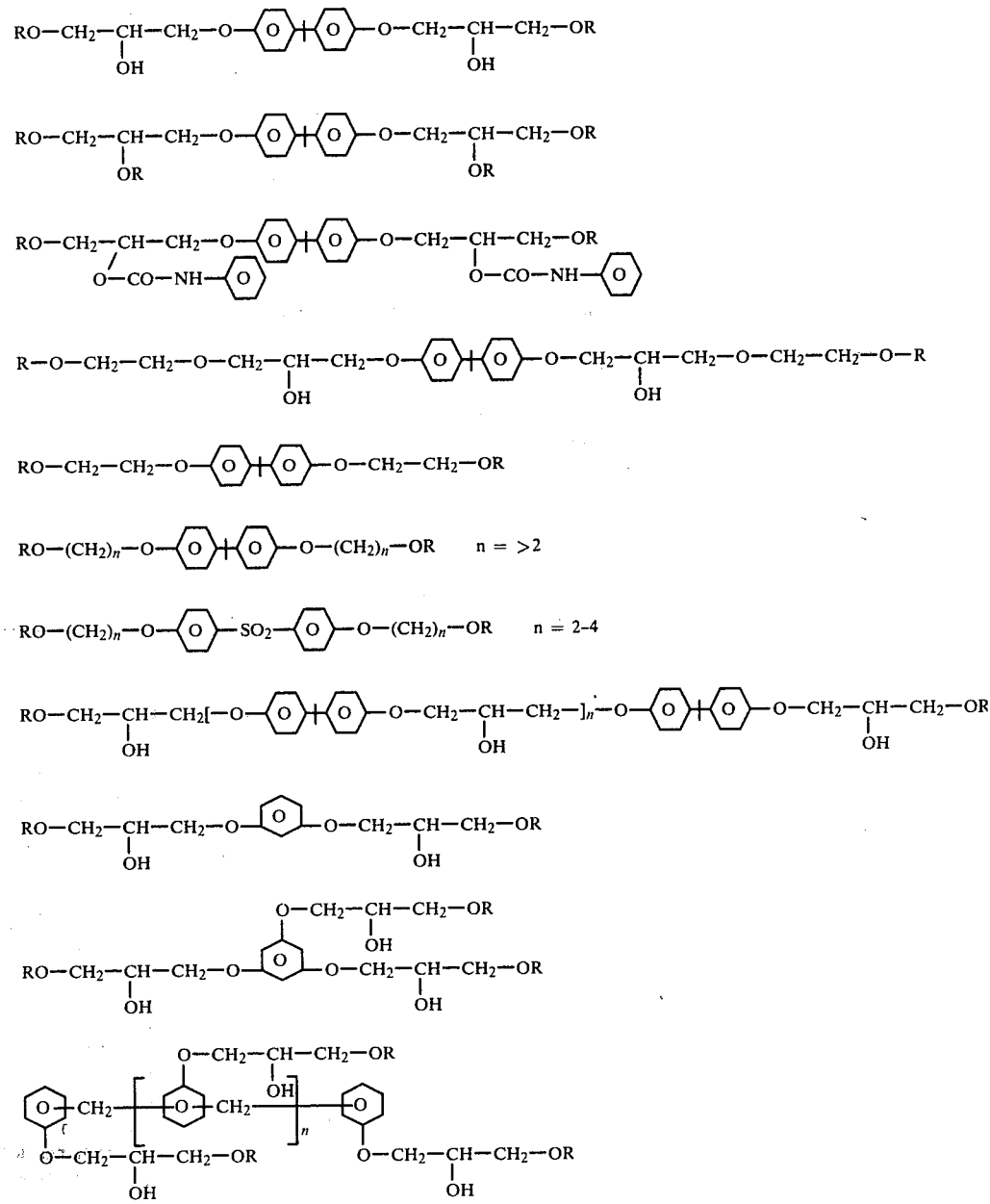

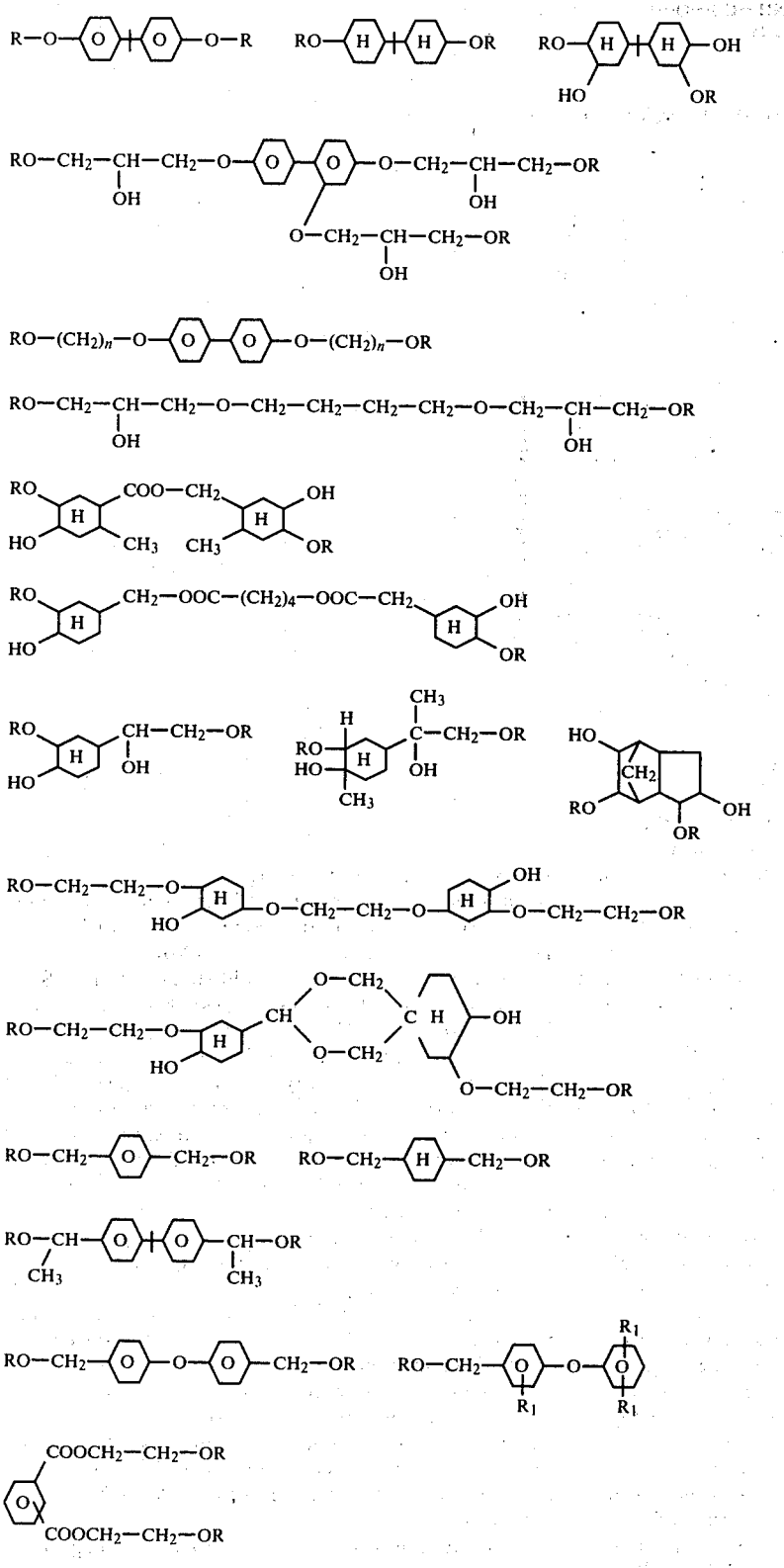
compounds, in the ortho-, meta- or para-form, of the formula
R—(O—D—O—X)$_n$—OD—OR
wherein
HO—D—OH is a polyol and
HO—X—OH is a dicarboxylic acid, and in particular in each case saturated or unsaturated and cyclic or acylic,

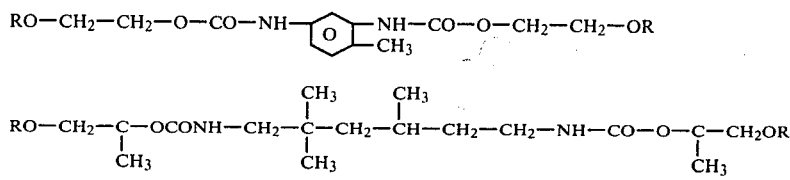

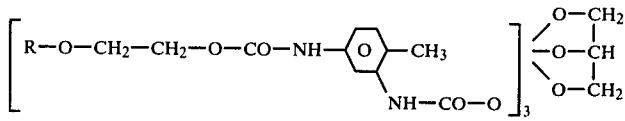

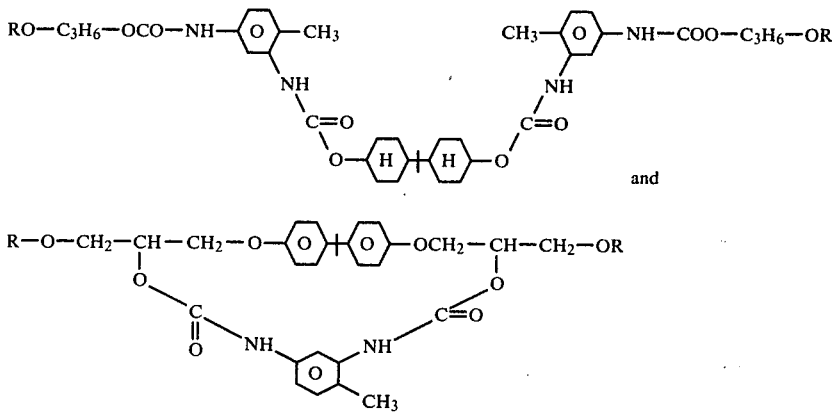
, (average molecular weight: 2,500)

and

Prepolymers which contain NCO groups or urethane groups and have been reacted with hydroxyalkyl methacrylate according to U.S. Pat. No. 4,089,763 or U.S. Pat. No. 3,425,988 are also suitable.

The number of oxyalkyl groups introduced into compounds of formula (Id), as indicated, is 1 to 10. The preferred range of n+m is 1 to 4 for composite dental filling compositions and 2 to 10 for coating and sealing compositions and for prothesis materials.

Suitable catalysts for the polymerisation of the monomers or monomer mixture mentioned to give the dental compositions according to the invention are, inter alia, peroxides or azo compounds, in particular benzoyl peroxide, o-toluyl peroxide, chlorobenzoyl peroxide, lauroyl peroxide, cumene hydroperoxide, t-butyl hydroperoxide or azodiisobutyric acid dinitrile. If the polymerisation is to be carried out at room temperature or in the mouth, the known redox systems or UV light or visible light in combination with photoinitiators are used.

As is known, the redox systems consist of an oxidising agent and a reducing agent, free radicals being formed when they react. Peroxide in combination with amines, mercaptans, sulphinic acids, aminosulphones or methylene-active compounds, such as N,N-dimethyl-5-isobutylbarbituric acid, are in general used. Examples of suitable amines are N,N-dimethyl-p-toluidine, N,N-dimethyl-3,5-dimethylaniline, N,N-bis-hydroxyalkyl-p-toluidines, N,N-bis-hydroxyalkyl-3,5-dimethylanilines, N,N-bis-hydroxyalkyl-3,5-di-tert.-butylanilines or N,N-bis-hydroxyalkyl-3,4-dimethylanilines.

Examples of suitable photoinitiators for the UV polymerisation are benzoin, benzoin ethers, α-acyloxime esters, acetophenone derivatives, such as 2,2-diethoxyacetophenone, benzil dimethyl ketal, esters of phenylglyoxylic acid, halogenated aromatic compounds, such as 4-tert.-butyl-2,2,2-trichloroacetophenone or 2-chlorothioanthone, and furthermore ketone/amine combinations, such as Michlers ketone or benzophenone and N-methyldiethanolamine. Such ketone/amine combinations are described, for example, in U.S. Pat. 3,759,807.

The monomer of formula (Id) for use according to the invention are especially suitable for use in the dental field, for example for the preparation of dental filling agents, dental repair materials, coating compositions, sealing compositions for cavities, materials for crowns, bridges and caps, prothesis materials, dentures and orthodonotic devices.

The form in which they are presented depends on the intended use. Thus, for example, two-component or one-component systems can be used for the preparation of dental filling materials. In the case of the two-component systems, the constituents of the redox system are distributed between the two components, which can be in a liquid or pasty form. A pasty consistency is achieved, for example, by admixing inorganic or organic fillers, bead polymers or pigments. Other additives which are frequently used are antioxidants, to prevent premature polymerisation, UV stabilisers or colorants.

However, the two components can also be kept separately in a mixing capsule (see, for example German Patent No. 1,566,294 or German Patent No. 2,324,296). Before use, the components are combined in the capsule and mixed on a shaking machine.

Advantageous one-component systems contain the monomers of formula (Id), if appropriate fillers, colorants and antioxidants, and furthermore photoinitiators for UV light or visible light.

According to the present invention there is further provided a method of filling or repairing teeth in warm-blooded animals in which the filling material or repair material is a dental composition of the invention. The invention also relates to dentures or other orthodontic devices when formed wholey or partially of a dental composition of the invention. The invention further relates to the dental composition of the invention for use in dental treatment.

The invention is illustrated by the following Examples.

EXAMPLE A

Instructions for the preparation of the oxyalkylated bis-hydroxy-methyl-tricyclo-[5.2.0.2.$^{2.6}$]-decane (a compound of formula (Ic))-(TCD—DM)

Product A:TCD—DM+2 mols of ethylene oxide 4,830 g of bishydroxymethyl-tricyclo-[5.2.0.1.$^{2.6}$] decane (TCD-DM; mixture of the 3,8-, 3,9- and 4,8-isomers) and 600 g of toluene are initially introduced into a stirred autoclave which could be heated and is provided with a device for azeotropic removal of the water, and the air is replaced by nitrogen. 70 g of 50% strength aqueous potassium hydroxide solution are added at 80° C. and 46 g of water is removed from the reaction mixture at 100°–115° C. by azeotropic distillation. 2,170 g of ethylene oxide are then slowly metered in at 100°–115° C. and under 0.4–0.6 bar and the mixture is subsequently stirred at 100°–105° C. for 3 hours. The alkaline reaction product is neutralised with 700 g of water and 245 g of 12.5% strength aqueous sulphuric acid. After adding a filtration auxiliary and an antioxidant, such as 0.05% of 2,6-bis-tert.-butyl-p-cersol, the water is then distilled off in vacuo at 70°–90° C. and the salts which has separated is filtered off, together with the filtration auxiliary. The neutral product thus obtained has a hydroxyl number of 383 and a viscosity $\eta_{25° C.}$ of 3,550 mPas.

The following hydroxyalkylation products of bishydroxymethyl-tricyclo-[5.2.0.1.$^{2.6}$]-decane (TCD-DM) are prepared analogously.

Product B: TCD-DM+4 mols of ethylene oxide; starting materials: 3,688 g of TCD-DM+3,312 g of ethylene oxide; OH number: 289; $\eta_{25° C.}$=980 mPas.

Product C: TCD-DM+8 mols of ethylene oxide; starting materials: 2,504 g of TCD-DM+4,496 g of ethylene oxide; OH number: 187; $\eta_{25° C.}$=480 mPas.

Product D: TCD-DM=2 mols of propylene oxide; starting materials: 4,398 g of TCD-DM+2,602 g of propylene oxide; OH number: 341; $\eta_{25° C.}$=5,080 mPas.

Product E: TCD-DM+4 mols of propylene oxide; starting materials: 3,206 g of TCD-DM+3,794 g of propylene oxide; OH number: 255; viscosity: $\eta_{25° C.}$=1,330 mPas.

EXAMPLE 1

Methacrylic acid ester of Product A:

1,460 g of product A, 15 g of methylene blue, 50 g of p-toluenesulphonic acid, 1,150 g of distilled methacrylic acid and 2,000 ml of toluene are heated to the boiling point, whilst bubbling in air. The water which forms is removed by azeotropic distillation. After 8 hours, the splitting off of water has ended. After cooling, the mixture is stirred for 1 hour with 40 g of bleaching earth in order to adsorb the methylene blue and the blue-coloured bleaching earth is filtered off. The filtrate is neutralised with excess sodium carbonate solution until the pH value is 8, and is filtered over a filtration auxiliary, such as cellulose flour. The upper phase is separated off, washed with sodium chloride solution and, after adding a polymerisation inhibitor, concentrated in vacuo until no further toluene is present.

Yield: 1,817 g; saponification number 268 (theory: 262); OH number: 5.6; viscosity: $\eta_{25° C.}$=104 mPas; refractive index: $n_D^{20}$=1.4925.

EXAMPLE 2

Methacrylic acid ester of Product B:

Analogously to Example 1, 1,940 g of product B, 15 g of methylene blue, 50 g of p-toluenesulphonic acid, 1,150 g of methacrylic acid and 2,000 ml of toluene are esterified and worked up.

Yield: 2,364 g; saponification number: 224 (theoretical: 216); OH number: 2.3; viscosity: $\eta_{25° C.}$=118 mPas at 13 dynes/cm$^2$; refractive index: $n_D^{20}$=1,4880.

EXAMPLE 3

Methacrylic acid ester of Product C:

Analogously to Example 1, 2,950 g of methacrylic acid ester with the following characteristics are obtained from 3,000 g of product C: saponification number: 154 (theoretical: 153); OH number: 5.1; viscosity: $\eta_{25° C.}$=157 mPas; $n_D^{20}$=1.4825.

EXAMPLE 4

Methacrylic acid ester of Product D:

4,051 g of the methacrylic acid ester are obtained from 3,280 g of product D; saponification number: 254; viscosity: $\eta_{25° C.}$=116 mPas; $n_D^{20}$=1.4840.

EXAMPLE 5

Methacrylic acid ester of Product E:

2,918 g of the corresponding methacrylic acid ester are obtained from 2,600 g of product E; saponification number 197 (theoretical: 196); OH number: 9.4; viscosity: $\eta_{25° C.}$=143 mPas; refractive index: $n_D^{20}$=1.4800.

The corresponding acrylic acid esters could also be prepared analogously to Examples 1–5.

EXAMPLE 6

Using the monomers prepared according to Example 1, a paste containing an aromatic amine (A paste) and a paste containing benzoyl peroxide (B paste) are prepared. In a ball-mill equal parts of these two pastes are mixed intimately for about 40 seconds, and test pieces are prepared from the mixture and are stored at 37° C. The physical properties of the test pieces are measured.

Paste 6 A 20.66 parts of the monomer according to Example 1, 0.30 part of N,N-bis-hydroxypropyl-3,5-dimethyl-aniline, 0.04 part of methacryloxypropyl-trimethoxysilane, 77.60 parts of a finely divided lanthanum-containing glass ceramic according to U.S. Pat. No. 4,017,454*, pre-treated with 0.4% of methacryloxypropyl-trimethoxysilane, and 1.40 parts of highly disperse silicic acid.

*The composition of the glass ceramic according to U.S. Pat. No. 4,017,454, corresponding to German Pat. No. 2,347,591 is: 4% of Li$_2$O; 3% of ZnO; 15% of La$_2$O$_3$; 19% of Al$_2$O$_3$; 46% of SiO$_2$; 5% of ZrO$_2$; 5% of P$_2$O$_5$; and 3% of Ta$_2$O$_5$;

Paste 6 B 17.7 parts of the monomer according to Example 1, 0.36 part of benzoyl peroxide, 0.04 part of methacryloxypropyl-trimethoxysilane, 80.69 parts of ground rock crystal, pre-treated with 0.04% of methacryloxypropyl-trimethoxysilane, and 1.21 parts of highly disperse silicic acid.

Physical parameters of the test pieces
Compressive strength: 224±8.5 N/mm$^2$
Flexural strength: 103±7.5 MPa
E modulus: 12,975±1,447 MPa

EXAMPLE 7

Analogously to Example 6, the following pastes are mixed using the monomers from Example 2 and test pieces are produced from the pastes.

Paste 7 A 21.58 parts of monomer from Example 2, 0.26 part of bis-propoxylated 3,5-dimethylaniline, 0.04 part of methacryloxypropyl-trimethoxysilane, 76.67 parts of finely divided lanthanum-containing glass ceramic according to U.S. Pat. No. 4,017,454 pre-treated with 0.4% of methacryloxypropyl-trimethoxysilane, and 1.45 parts by highly disperse silicic acid

Paste 7 B 19.59 parts of the monomer according to Example 2, 0.40 part of benzoyl peroxide, 0.20 part of methacryloxypropyl-trimethoxysilane, 78.46 parts of finely divided rock crystal, pre-treated with 0.4% of methacryloxypropyl-trimethoxysilane, and 1.35 parts of highly disperse silicic acid.

The compressive strength of the test piece is 184.2±5.92 N/mm$^2$.

EXAMPLE 8

Analogously to Example 6, the following pastes are mixed using the monomer from Example 3 and test pieces are produced from these parts.

Paste 8 A 21.53 parts of the monomer according to Example 3, 0.30 part of bis-propoxylated 3,5-dimethylaniline, 0.04 part of methacryloxypropyl-trimethoxysilane, 76.67 parts of silanised lanthanum-containing glass ceramic according to U.S. Pat. No. 4,017,454 and 1.46 parts of highly disperse silicic acid.

Paste 8 B 17.00 parts of the monomer according to Example 3, 0.34 part of benzoyl peroxide, 0.04 part of methacryloxypropyl-trimethoxysilane, 81.13 parts of finely divided rock crystal, pre-treated with 0.4% of methacryloxypropyl-trimethoxysilane and 1.44 parts of highly disperse silicic acid.

The test pieces produced from equal parts of paste A and B have the following physical properties.
Compressive strength: 120.4±6 N/mm$^2$
Flexural strength: 21.5±9 MPa

EXAMPLE 9

Analogously to Example 6, the monomer prepared according to Example 4 is mixed to form the following pastes and test pieces are produced from these pastes.

Paste 9 A 22.30 parts of the monomer according to Example 4, 0.32 part of bis-propoxylated 3,5-dimethylaniline, 0.04 part of methacryloxypropyl-trimethoxysilane, 0.07 part of 2-hydroxy-4-methoxy-benzophenone, 76.00 parts of silanised La glass ceramic according to U.S. Pat. No. 4,017,454 and 1.27 parts of highly disperse silicic acid.

Paste 9 B 22.32 parts of the monomer according to Example 4, 0.46 part of benzoyl peroxide, 0.04 part of methacryloxypropyl-trimethoxysilane, 0.06 part of 2-hydroxy-4-methoxy-benzophenone, 75.93 parts of silanised finely divided rock crystal and 1.19 parts of highly disperse silicic acid.

Compressive strength: 185.5 N/mm$^2$
Flexural strength: 86.8 MPa
Deflection: 0.28 mm
E modulus: 10,930 MPa

EXAMPLE 10

Analogously to Example 6, test pieces are produced from the following pastes and tested. The pastes are mixed using the monomer according to Example 5.

Paste 10 A 20.66 parts of the monomer according to Example 5, 0.30 part of bis-hydroxypropylated 3,5-dimethylaniline, 0.04 part of methacryloxypropyl-trimethoxysilane, 77.60 parts of silanised La glass ceramic according to U.S. Pat. No. 4,017,454 and 1.40 parts of highly disperse silicic acid.

Paste 10 B 18.34 parts of the monomer according to Example 5, 0.37 part of benzoyl peroxide, 0.04 part of methacryloxypropyl-trimethoxysilane, 80.00 parts of finely divided silanised rock crystal and 1.25 parts of highly disperse silicic acid.

Test pieces are produced by mixing equal parts by weight of pastes 10 A and 10 B, and after storage in water at 37° C. for 24 hours, these test pieces have the following test values.
Compressive strength: 180±11 N/mm
Flexural strength: 94±7 MPa
E modulus: 10,400±785 MPa

EXAMPLE 11

A monomer mixture is prepared by mixing 80 parts of the monomer according to Example 2 with 20 parts of trimethylolpropane trimethacrylate. The pastes 11 A and 11 B prepared therefrom are processed in the ratio 1:1 to form test pieces.

Paste 11 A 17.20 parts of the monomer according to Example 2, 4.30 parts of trimethylolpropane trimethacrylate, 0.30 part of N,N-bis-hydroxypropyl-3,5-dimethylaniline, 0.04 part of methacryloxypropyl-trimethoxysilane, 0.06 part of 2-hydroxy-4-methoxy-benzophenone, 76.64 parts of La-containing silanised glass ceramic according to U.S. Pat. No. 4,017,454 and 1.46 parts of highly disperse silicic acid.

Paste 11 B 14.88 parts of the monomer according to Example 2, 3.70 parts of trimethylolpropane trimethacrylate, 0.38 parts of benzoyl peroxide, 0.04 part of methacryloxypropyl-trimethoxysilane, 0.06 part of 2-hydroxy-4-methoxy-benzophenone, 79.49 parts of silanised finely divided rock crystal and 1.45 parts of highly disperse silicic acid.

Compressive strength: 198±13 N/mm$^2$

Flexural strength: 104±6 MPa
E modulus: 12,900±2,078 MPa

EXAMPLE 12

A monomer mixture is prepared from equal parts by weight of the monomer prepared according to Example 3 and a urethane methacrylate, which is prepared from 1 mol of trimethyl-hexamethylene-diisocyanate and 2 moles of β-hydroxyethyl methacrylate and is called Plex 666-1 in the following test.

Paste 12 A 10.79 parts of the monomer according to Example 3, 10.79 parts of Plex 666-1, 0.21 part of N,N-bis-hydroxypropyl-3,5-dimethylaniline, 0.04 part of methacryloxypropyl-trimethoxysilane, 0.06 part of 2-hydroxy-4-methoxy-benzophenone, 76.71 parts of silanised La glass ceramic according to U.S. Pat. No. 4,017,454 and 1.40 parts of highly disperse silicic acid.

Paste 12 B 10.67 parts of the monomer according to Example 3, 10.67 parts of Plex 666-1, 0.45 part of benzoyl peroxide, 0.06 part of 2-hydroxy-4-methoxy-benzophenone, 0.04 part of methacryloxypropyl-trimethoxysilane, 76.71 parts of silanised finely divided rock crystal and 1.40 parts of highly disperse silicic acid.

The test pieces produced from equal parts of pastes 12 A and 12 B have the following strength after storage in water for 24 hours.
Compressive strength: 198±14 N/mm$^2$
Flexural strength: 94±4 MPa
E modulus: 6,956±135 MPa

EXAMPLE 13

A monomer mixture of 72 parts of the monomer according to Example 5 and 28 parts of trimethylolpropane trimethacrylate is used. Analogously to Example 6, pastes 13 A and 13 B are mixed and are hardened in the weight ratio 1:1 to give test pieces.

Paste 13 A 16.05 parts of the monomer according to Example 5, 6.23 parts of trimethylolpropane trimethacrylate, 0.33 part of N,N-bis-hydroxypropyl-3,5-dimethylaniline, 0.04 part of methacryloxypropyl-trimethoxysilane, 75.76 parts of silanised La-containing glass ceramic according to U.S. Pat. No. 4,017,454 and 1.52 parts of highly disperse silicic acid.

Paste 13 B 13.38 parts of the monomer according to Example 5, 5.20 parts of trimethylolpropane trimethacrylate, 0.38 part of benzoyl peroxide, 0.04 part of methacryloxypropyl-trimethoxysilane, 0.06 part of 2-hydroxy-4-methoxy-benzophenone, 79.49 parts of silanised finely divided rock crystal and 1.45 parts of highly disperse silicic acid.
Compressive strength: 172±17 N/mm$^2$
Flexural strength: 86±23 MPa
E modulus: 10,886±702 MPa

EXAMPLE 14

Example 6 is repeated with a mixture of 70 parts of monomer 5 and 30 parts of 2,2-propane-bis-[3-(4-phenoxy)-1,2-dihydroxypropane-1-methacrylate]. The latter monomer is also called BIS-GMA.

Paste 14 A 17.70 parts of the monomer from Example 5, 4.70 parts of BIS-GMA, 0.23 part of N,N-bis-hydroxypropyl-3,5-dimethylaniline, 0.04 part of methacryloxypropyl- trimethoxysilane, 0.06 part of 2-hydroxy-4-methoxy- benzophenone, 76.00 parts of La-containing glass ceramic according to U.S. Pat. No. 4,017,454 pretreated with 0.4% of methacryloxypropyl-trimethylsilane and 1.27 parts of highly disperse silicic acid.

Paste 14 B 15.10 parts of the monomer according to Example 5, 6.50 parts of BIS-GMA, 0.43 part of benzoyl peroxide, 0.04 part of methacryloxypropyl-trimethoxysilane, 0.06 part of 2-hydroxy-4-methoxy-benzophenone, 76.72 parts of finely divided rock crystal, pre-treated with 0.4% of methacryloxypropyl-trimethoxysilane and 1.15 parts of highly disperse silicic acid.

The test pieces produced from equal parts of pastes 14 A and 14 B have the following physical properties.
Compressive strength: 180.9 N/mm$^2$
Flexural strength: 77.9 MPa
E modulus: 10,680 MPa

EXAMPLE 15

Example 6 is repeated with a mixture of 50 parts of the monomer according to Example 1 and 50 parts of a urethane methacrylate which have been prepared from 1 mol of trimethylhexamethylene diisocyanate and 2 moles of β-hydroxy-ethyl methacrylate (Plex 666-1). 0.2% of methacryloxypropyl-trimethoxysilane and 0.3% of 2-hydroxy-4-methoxybenzophenone also added to the monomer mixture.

Paste 15 A 22.50 parts of the monomer mixture, 0.23 part of N,N-bis-hydroxypropyl-3,5-dimethylaniline, 76.00 parts of silanised La-containing glass ceramic according to U.S. Pat. No. 4,017,454 and 1.27 parts of highly disperse silicic acid.

Paste 15 B 22.40 parts of the monomer mixture, 0.46 part of benzoyl peroxide, 0.02 part of 2,6-di-tert.-butyl-4-cresol, 75.93 parts of silanised finely divided rock crystal and 1.19 parts of highly disperse silicic acid.

The test pieces produced from equal parts of pastes 15 A and 15 B have the following level of strength:
Compressive strength: 196.7 N/mm$^2$
Flexural strength: 87.6 MPa
E modulus: 11,700 MPa

EXAMPLE 16

Example 6 is repeated with a mixture of 70 parts of the monomer prepared according to Example 1 and 30 parts of BIS-GMA, 0.2% of methacryloxypropyl-trimethoxysilane, 0.3% of 2-hydroxy-4-methoxy-benzophenone and 0.075% of 2,6-di-tert.-butyl-4-cresol are also added to the mixture.

Paste 16 A 22.50 parts of stabilised monomer mixture, 0.23 part of N,N-bis-hydroxypropyl-3,5-dimethylaniline, 76.00 parts of La-containing silanised glass ceramic according to U.S. Pat. No. 4,017,454 and 1.27 parts of highly disperse silicic acid.

Paste 16 B 22.42 parts of stabilised monomer mixture, 0.46 part of benzoyl peroxide, 75.93 parts of silanised finely divided rock crystal and 1.19 parts of highly disperse silicic acid.

The strength values of the test pieces produced from pastes 16 A and 16 B are:
Compressive strength: 192.5 N/mm²
Flexural strength: 80.0 MPa
E modulus: 12,420 MPa

Example 17

Example is repeated with a mixture of equal parts of the monomer according to Example 2 and the reaction product of 1 mole of trimethyl-hexamethylene diisocyanate and 2 moles of β-hydroxy-ethyl methacrylate. Before preparing the pastes, 0.2% methacryloxypropyl-trimethoxysilane and 0.3% of 2-hydroxy-4-methoxybenzophenone are also added to the mixture.

Paste 17 A 22.50 parts of stabilised monomer mixture, 0.23 part of bis-hydroxypropyl-3,5-dimethylaniline, 76.00 parts of silanised La-containing glass ceramic and 1.27 parts of highly disperse silicic acid.

Paste 17 B 22.42 parts of monomer mixture, 0.01 part of 2,6-di-tert.-butyl-4-cresol, 0.45 part of benzoyl peroxide, 75.93 parts of silanised finely divided rock crystal and 1.19 parts of highly disperse silicic acid.

Equal parts by weight of pastes 17 A and 17 B are processed to test pieces.
Compressive strength: 178.5 N/mm²
Flexural strength: 91.3 MPa
E modulus: 10,710 MPa

EXAMPLE 18

Example 6 is repeated with a mixture of 70 parts of the monomer according to Example 2 and 30 parts of BIS-GMA; the mixture additionally contained 0.2% of methacryloxypropyl-trimethoxysilane, 0.3% of 2-hydroxy-4-methoxy-benzophenone and 0.05% of 2,6-di-tert.-butyl-4-cresol.

Paste 18 A 22.50 parts of stabilised monomer mixture, 0.23 part of N,N-bis-hydroxypropyl-3,5-dimethylaniline, 76.00 parts of silanised La-containing glass ceramic according to U.S. Pat. No. 4,017,454 and 1.27 parts of highly disperse silicic acid.

Paste 18 B 22.42 parts of stabilised monomer mixture, 0.46 part of benzoyl peroxide, 75.93 parts of silanised finely divided quartz and 1.19 parts of highly disperse silicic acid.

The test pieces produced from equal amounts by weight of pastes 18 A and 18 B have the following strength values:
Compressive strength: 188.6 N/mm²
Flexural strength: 76.2 MPa
E modulus: 10,720 MPa

EXAMPLE 19

To prepare an X-ray opaque dental filling composition which could be hardened with UV light, a paste is mixed from the following components: 22.73 parts of the monomer according to Example 4, containing 0.2% of methacryloxypropyl-trimethoxysilane, 0.28 part of benzil dimethyl ketal, 37.78 parts of silanised La-containing glass ceramic according to U.S. Pat. No. 4,017,454, 37.78 parts of silanised glass ceramic based on my-Cordierite and 1.43 parts of highly disperse silicic acid. On irradiation with a commercially available UV-polymerisation apparatus, a polymerisation depth of 2.2 mm is achieved after 20 seconds.

The compressive strength of a test pieces is 203.0 N/mm².

EXAMPLE 20 (Comparison experiment)

For comparison, pastes are prepared with the methacrylic acid ester, prepared according to German Patent No. 2,816,823, Example 1, of bis-hydroxymethyl-tricyclo-[5.2.1.0²·⁶]-decane. The monomer is stabilised with 0.2% of methacryloxypropyl-trimethoxysilane and 0.3% of 2-hydroxy-4-methoxy-benzophenone and processed to the following pastes:

Paste 20 A 22.40 parts of stabilised TCD-DM methacrylate, 0.32 part of N,N-bis-hydroxypropyl-3,5-dimethylaniline, 75.76 parts of La-containing glass ceramic according to U.S. Pat. No. 4,017,454, pre-treated with 0.4% of methacryloxypropyl-trimethoxy-silane and 1.52 parts of highly disperse silicic acid.

Paste 20 B 18.67 parts of stabilised TCD-DM methacrylate, 0.39 part of benzoyl peroxide, 79.49 parts of finely divided rock crystal, pre-treated with 0.4% of methacryloxypropyl-trimethylsilane, and 1.45 parts of highly disperse silicic acid.

Test pieces are produced by mixing equal parts of the two pastes 20 A and 20 B and these test pieces harden in about 3 minutes. After storage in water at 37° C. for 24 hours, the following physical parameters are found:
Compressive strength: 216.7±28.3 N/mm²
Flexural strength: 82.8±17.9 MPa
Deflection: 0.19±0.02
E modulus: 15,300±2,107 MPa

What is claimed is:
1. A dental composition comprising a polymerisable (meth)acrylic acid ester of the formula

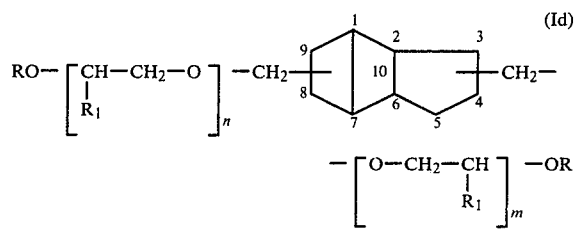

in which
R represents

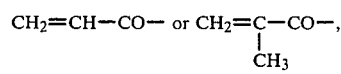

$R_1$ represents a hydrogen atom or a methyl or ethyl group, and $n+m$ represents a number from 1 to 10; and one or more inert dentally acceptable carriers.

2. A dental composition according to claim 1 wherein said inert dentally acceptable carriers include fillers, stabilisers or pigments.

3. A dental composition according to claim 1 or 2 in which R represents

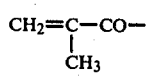

4. A dental composition according to claim 3 in which $R_1$ represents a hydrogen atom.

5. A dental composition according to claim 3 in which $R_1$ represents a methyl group.

6. A dental composition according to claim 1 wherein $R_1$ represents hydrogen and $n+m$ represents the integer 2.

7. A dental composition according to claim 1 wherein $R_1$ represents hydrogen and $n+m$ represents the integer 4.

8. A dental composition according to claim 1 wherein $R_1$ represents hydrogen and $n+m$ represents the integer 8.

9. A dental composition according to claim 1 wherein $R_1$ represents a methyl group and $n+m$ represents the integer 2.

10. A dental composition according to claim 1 wherein $R_1$ represents a methyl compound and $n+m$ represents the integer 4.

11. A dental composition according to claim 1 or 2 in which the polymerisable (meth)acrylic acid ester of formula (Id) is mixed with another polyfunctional monomer.

12. A dental composition according to claim 11 in which the other polyfunctional monomer is a polymerisable di-(meth)acrylic acid ester.

13. A method of filling or repairing teeth in warm-blooded animals in which the filling material or repair material is a dental composition as claimed in claim 1.

14. A method according to claim 13 in which the polymerisable (meth)acrylic acid ester is one in which R represents

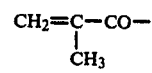

15. A method according to claim 14 in which the polymerisable (meth)acrylic acid ester is one in which $R_1$ represents a hydrogen atom.

16. A method according to claim 14 in which the polymerisable (meth)acrylic acid ester is one in which $R_1$ represents a methyl group.

17. A denture or other orthodontic device when formed wholly or partially of a dental composition as claimed in claim 1.

* * * * *